(12) United States Patent
Peterson et al.

(10) Patent No.: US 6,755,812 B2
(45) Date of Patent: Jun. 29, 2004

(54) DEFLECTABLE TELESCOPING GUIDE CATHETER

(75) Inventors: Charles R. Peterson, Murrieta, CA (US); Frank E. Manning, Valley Center, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/014,735

(22) Filed: Dec. 11, 2001

(65) Prior Publication Data

US 2003/0109852 A1 Jun. 12, 2003

(51) Int. Cl.⁷ .......................... A61M 25/01; A61N 1/00
(52) U.S. Cl. .................................. 604/528; 607/122
(58) Field of Search ........................ 604/523, 528, 604/530, 534, 164.01, 164.13, 165.05, 96.01; 607/122

(56) References Cited

U.S. PATENT DOCUMENTS

| | | | |
|---|---|---|---|
| 4,777,951 A | * 10/1988 | Cribier et al. | 128/344 |
| 4,898,577 A | * 2/1990 | Badger et al. | 604/53 |
| 5,290,229 A | 3/1994 | Paskar | |
| 5,318,528 A | 6/1994 | Heaven et al. | |
| 5,389,090 A | * 2/1995 | Rischell et al. | 604/280 |
| 5,423,772 A | 6/1995 | Lurie et al. | |
| 5,488,960 A | 2/1996 | Toner | |
| 5,497,784 A | * 3/1996 | Imran | 128/772 |
| 5,676,653 A | * 10/1997 | Taylor | 604/95 |
| 5,775,327 A | 7/1998 | Randolph et al. | |
| 5,882,333 A | 3/1999 | Schaer et al. | |
| 5,902,289 A | * 5/1999 | Swartz et al. | 604/281 |
| 6,021,340 A | 2/2000 | Randolph et al. | |
| 6,066,126 A | * 5/2000 | Li et al. | 604/532 |
| 6,086,548 A | * 7/2000 | Chaisson et al. | 600/585 |
| 6,251,104 B1 | 6/2001 | Kesten et al. | |
| 6,277,107 B1 | 8/2001 | Lurie et al. | |
| 6,280,433 B1 | 8/2001 | McIvor et al. | |
| 6,408,214 B1 | 6/2002 | Williams et al. | |
| 6,530,914 B1 | * 3/2003 | Mickley | 604/528 |
| 2001/0039413 A1 | 11/2001 | Bowe | |

FOREIGN PATENT DOCUMENTS

DE 3819372 C1 4/1990

* cited by examiner

*Primary Examiner*—Angela D. Sykes
*Assistant Examiner*—B. Webb
(74) *Attorney, Agent, or Firm*—Crawford Maunu PLLC

(57) ABSTRACT

A catheter employs an inner guide with a pre-formed distal tip, an outer guide with a predetermined deflection location, and a proximal actuator. The inner guide can be longitudinally extended and axially rotated relative to the outer guide. The proximal actuator can adjustably change a bend angle of the predetermined deflection location. The catheter can be deployed with the inner guide retracted inside the distal end of the outer catheter. The extensible and rotatable inner catheter can be combined with the adjustable bend angle of the outer guide to provide an improved system for accessing and cannulating venous structures.

24 Claims, 7 Drawing Sheets

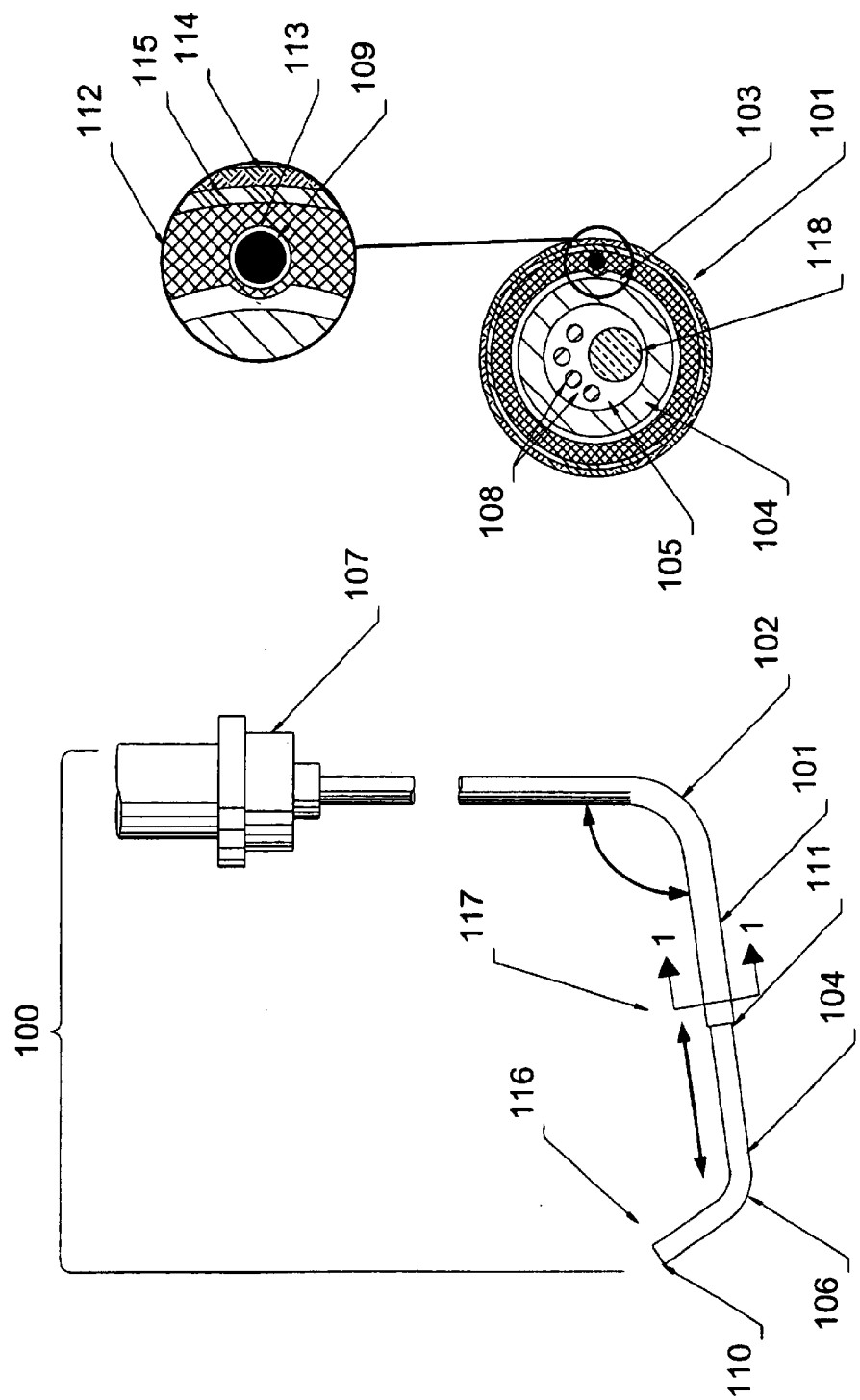

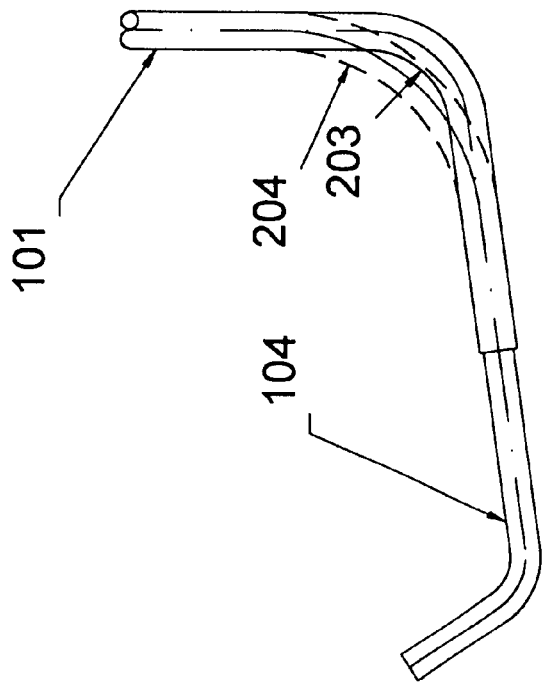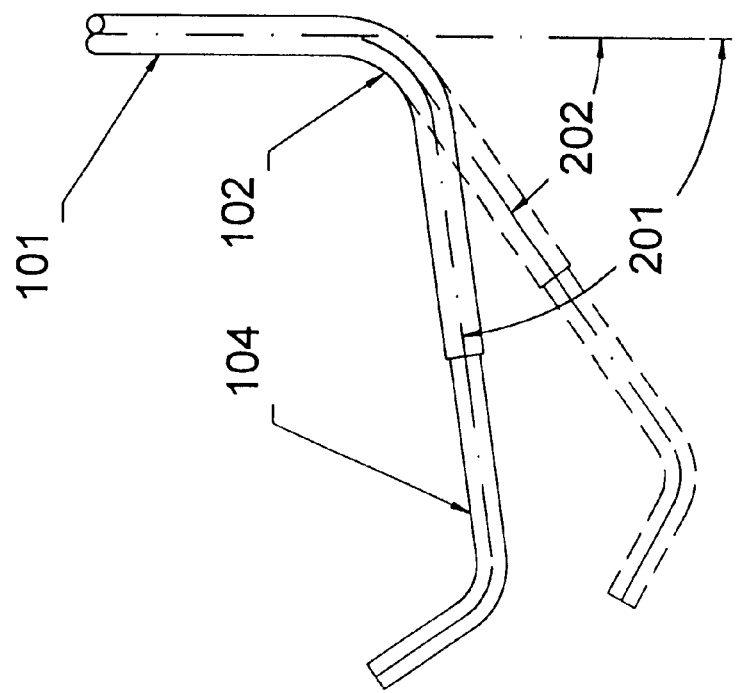

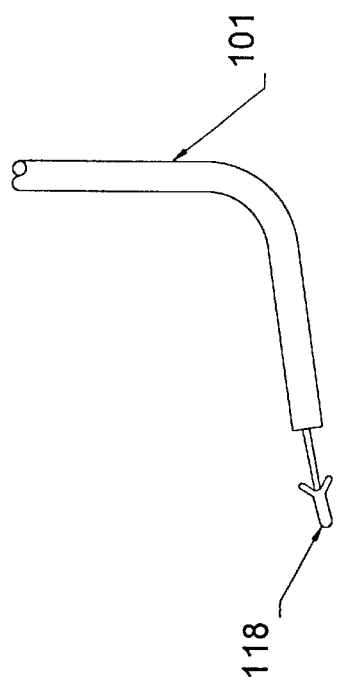
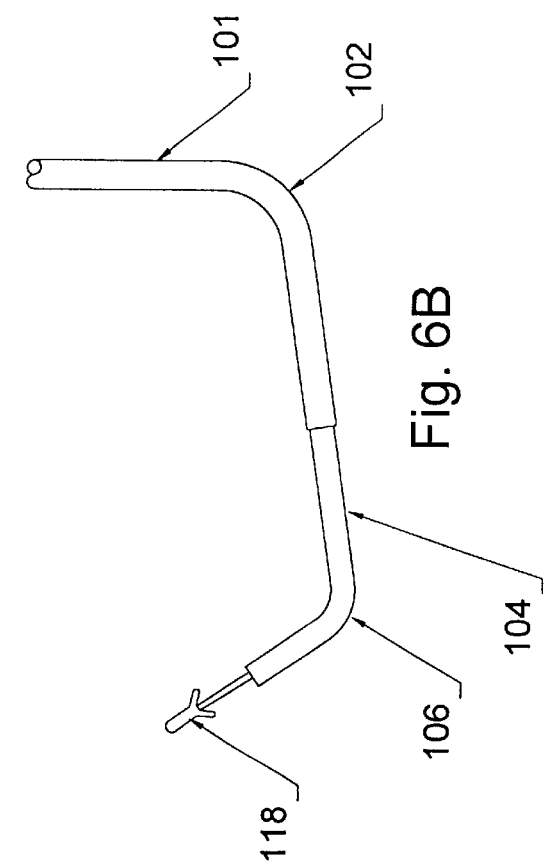

DEFLECTABLE TELESCOPING GUIDE CATHETER

FIELD OF THE INVENTION

The invention relates generally to guide catheters, and more particularly to steerable, telescoping guide catheters used to locate and cannulate the coronary sinus of a patient's heart.

BACKGROUND OF THE INVENTION

Guiding catheters are instruments that allow a physician to access and cannulate vessels in a patient's heart for conducting various medical procedures, including venography and implanting of cardiac pacing devices. Cannulating heart vessels requires navigating a small diameter, flexible guide through the tortuous vasculature into a heart chamber, and then into a destination heart vessel. Once the destination heart vessel is reached, the catheter acts as a conduit for insertion of payloads into the vessel.

A commonly accessed destination vessel for cardiac pacing lead insertion is the coronary sinus. A pre-shaped guiding catheter is typically used to blindly locate the coronary sinus ostium. This endeavor, however, is complicated by the fact that the location of the coronary sinus ostium may vary appreciably from one patient to another, especially among patients with diseased hearts. Oftentimes, the clinician is entirely unable to locate the coronary sinus ostium using the guiding catheter, and must resort to finding the ostium by "mapping" (interpreting localized bipolar waveforms) using an electrophysiological (EP) catheter and an ECG monitor. After the ostium is located, the guiding catheter is typically used to inject radiographic contrast media into the coronary sinus to highlight the associated venous system, and then a pacing lead is installed within one of the coronary branches.

Complicating this scenario is the dynamic structural deformation of the heart chambers that occurs from normal cardiac activity during the procedure. This further increases the difficulty of guiding a catheter to its destination. Presently, a considerable amount of time is often spent by the physician when manipulating such catheters within cardiac structures, such as the right atrium, simply trying to locate an anatomical feature of interest, such as the coronary sinus ostium.

Guiding catheter systems are typically configured with a profile that is optimized for the intended method of access. In the case of accessing the coronary sinus via the right atrium, a catheter with a distal contour including a relatively sharp bend will point the catheter towards the likely location of the coronary sinus once the right atrium is reached. The contours of pre-shaped guiding catheters are generally fixed, and this is typically achieved in production by constraining the distal end within a shaping fixture while warming them until they assume the intended shape (i.e., by "heat setting" their polymer shaft).

Guiding catheters are sometimes introduced over a pre-shaped guide wire that is inserted into the desired location first. The guide wire is typically small and maneuverable, and can be pre-shaped for the desired venous path. However, utilizing a guide wire prior to introducing the guide catheter is more time consuming as two operations are required. Shortening the time required to cannulate the desired vessels is desirable as it reduces the total procedure time and reduces trauma to the patient.

There is a need for an improved guide catheter having enhanced maneuvering capabilities for accessing blood vessels of interest and for cannulating those vessels. There exists a further need for a guiding catheter that accounts for anatomical variation and defects with the destination structures. The present invention fulfills these and other needs, and addresses other deficiencies of prior art implementations and techniques.

SUMMARY OF THE INVENTION

The present invention is directed to a guide catheter employing a telescoping inner guide and a deflectable outer guide. According to one embodiment of the present invention, the catheter includes an outer guide having a distal end, a proximal end, and a predetermined deflection location proximate the distal end. An inner guide section having an inner guide lumen and a pre-formed distal end is movably disposed within the outer guide. The inner guide section is displaceable beyond the distal end of the outer guide. An actuator mechanism located at the proximal end of the catheter changes a bend angle at the predetermined deflection location of the outer guide. The proximal end of the inner guide is accessible at the proximal end of the catheter allowing adjustable axial displacement of the pre-formed distal end of the inner guide relative to the outer guide.

In one configuration of the catheter, the inner guide can be axially displaced beyond the distal end of the outer guide within a range of 0 to about 20 centimeters. For example, at least 2 centimeters of the inner guide can be axially displaced beyond the distal end of the outer guide.

The pre-formed distal end of the inner guide may be configured to be deformable, such that the inner guide is retractable within the distal end of the outer guide. In one configuration, the inner guide is substantially more flexible than the outer guide, such that the distal end of the inner guide assumes the shape of the outer guide when the inner guide is retracted.

The bend angle at the predetermined deflection location of the outer guide can be defined relative to a longitudinal axis of the outer guide proximal to the predetermined deflection location. In one configuration, the bend angle can be adjustable from a minimum of about 0 degrees to a maximum of about 150 degrees.

A bend radius of the predetermined deflection location can be defined relative to a centerline of the predetermined deflection location. The bend radius is greater than about six times an outer diameter of the outer guide.

The inner guide is arranged such that axial forces exerted on the proximal end of the inner guide can extend and retract the pre-formed distal end of the inner guide relative to the distal end of the outer guide.

In one configuration, the catheter further includes at least one steering tendon connected to the inner guide proximate to the pre-formed distal end. The proximal actuator mechanism can produce a tensile force acting on the steering tendon(s). The tensile force acting on the steering tendon(s) imparts a change in the bend angle at the predetermined deflection location of the outer guide.

In another configuration, the catheter further includes at least one steering tendon connected to the outer guide proximate to the distal end. The actuator mechanism produces a tensile force acting on the steering tendon(s). The tensile force acting on the steering tendon(s) imparts a change in the bend angle at the predetermined deflection location of the outer guide.

The catheter may be configured such that an axial rotational force imparted on the proximal end of the outer guide rotates the pre-formed distal end of the inner guide. In one configuration of the invention, the catheter further includes a seal between the inner guide and the outer guide. The seal is typically located at the proximal end of the catheter.

According to a further embodiment of the present invention, the catheter further includes an occlusion balloon affixed to the distal end of the outer guide.

In one configuration, for example, the catheter further includes at least one electrode located proximate the pre-formed distal end of the inner guide. One or more electrical conductors can be coupled to the electrode(s) and extend through at least one of the inner and outer guide lumens to a proximal section of the catheter.

According to a further embodiment of the present invention, the catheter includes a plurality of band electrodes disposed at the distal end of at least one of the inner and outer guides. One or more electrical conductors can be coupled to the band electrode(s) and extend through at least one of the inner and outer guide lumens to a proximal section of the catheter.

According to another embodiment of the present invention, a method of inserting a payload into a coronary sinus of a patient's heart involves providing a catheter having an outer guide, an inner guide and an actuator mechanism. The outer guide includes an outer guide lumen, a distal end, a proximal end, and a predetermined deflection location proximate the distal end. The inner includes an inner guide lumen, a pre-formed distal end, and a proximal end. The inner guide is movable within the outer guide lumen and displaceable beyond the distal end of the outer guide. The actuator mechanism is located at a proximal end of the catheter. The actuator mechanism changes a bend angle at the predetermined deflection location of the outer guide. The proximal end of the inner guide is accessible at the proximal end of the catheter, allowing adjustable axial displacement of the pre-formed distal end of the inner guide relative to the distal end of the outer guide.

The method further involves inserting the distal end of the catheter through a patient's right atrium via an access vessel. The inner guide is distally displaced beyond the distal tip of the outer guide and the bend angle is changed at the predetermined deflection location via the actuator mechanism to direct the pre-formed distal end of the inner guide for finding and cannulating the patient's coronary sinus. The outer guide is distally advanced over the inner guide to seat the outer guide in the patient's coronary sinus. The inner guide is proximally retracted to remove the inner guide from the catheter. The payload is advanced through the proximal end of the outer guide such that the payload is inserted into the patient's coronary sinus. In one aspect of the method, the payload includes a cardiac pacing lead.

According to yet another embodiment of the present invention, a method of inserting a payload into a coronary sinus of a patient's heart involves inserting the distal end of the catheter through a patient's right atrium via an access vessel. The inner guide is distally displaced beyond the distal tip of the outer guide and the bend angle is changed at the predetermined deflection location via the actuator mechanism to direct the pre-formed distal end of the inner guide for finding and cannulating the patient's coronary sinus. The payload is advanced through the proximal end of the inner guide such that the payload is inserted into the patient's coronary sinus. In one aspect of the method, the payload includes a cardiac pacing lead.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 1B is an external view of a catheter embodying features of the present invention;

FIG. 1C is an axial cross section 1—1 from FIG. 1B showing the distal end of an outer guide;

FIG. 2A is a view of the distal end of the catheter showing adjustable bend angle of the preformed location on the outer guide;

FIG. 2B is a view of the distal end of the catheter showing varying bend radii of the preformed location on the outer guide;

FIG. 6A is an external view of the catheter showing pacing lead delivery from the outer guide after the inner guide has been removed; and FIG. 6B is an external view of the catheter showing pacing lead delivery from the inner guide.

Figure 1A:
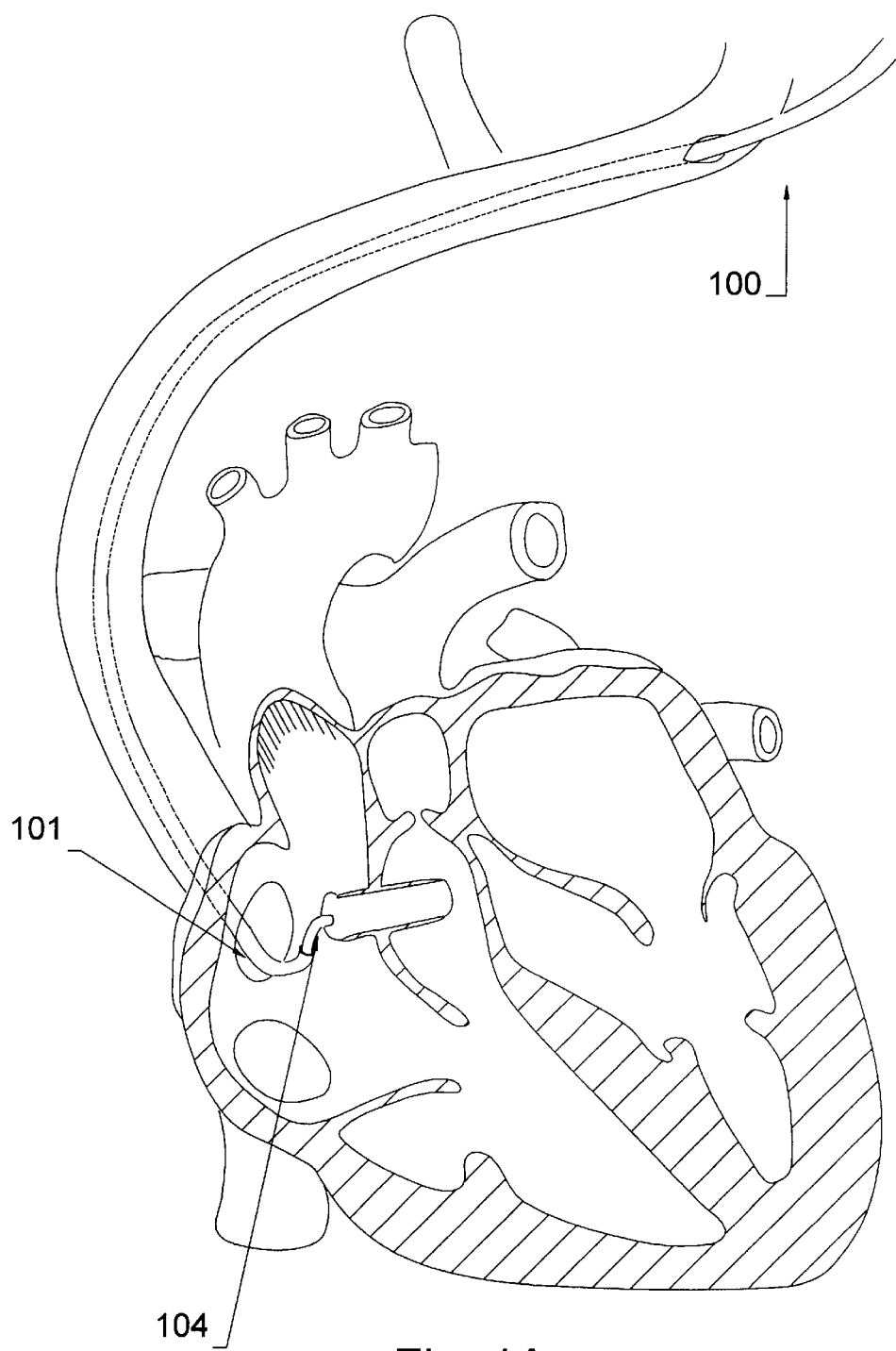
FIG. 1A is a cut-away view of a patient's heart, showing a catheter embodying features of the present invention deployed within the heart.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

With reference to FIG. 1A, a distal end of a catheter 100 is illustrated in accordance with an embodiment of the present invention. The catheter 100 includes an outer guide 101 and an inner guide 104. The catheter 100 is shown deployed within a patient's heart, accessing the coronary via the right atrium. A distal end of the inner guide 104 extends from the outer guide 101 as the inner guide 104 is advanced towards the coronary sinus ostium.

Turning now to FIGS. 1B and 1C, features of a catheter 100 accordance with an embodiment of the present invention are detailed. The catheter 100 includes an outer guide 101. The outer guide 101 is configured as an elongated, flexible shaft with a centrally disposed open lumen 103. The catheter 100 further includes an inner guide 104 that can be configured as an elongated flexible shaft with a central open lumen. The inner guide 104 is movably disposed within the open lumen 103 of the outer guide 101. The distal end of the inner guide 104 is shown in FIG. 1B extending beyond the distal tip 111 of the outer guide 101. The inner guide 104 can longitudinally extend and retract relative to the distal tip 111 of the outer guide 101.

The outer guide 101 includes a deflection location 102 at a distal section of the outer guide 101. An actuator 107 allows selectable shaping of the deflection location 102. The deflection location 102 is advantageously located at a pre-determined distance from the distal tip 111 of the outer guide to assist in navigation of the catheter 100. Once the outer guide 101 enters an access chamber (the right atrium of the heart, for example) the distal tip 110 of the inner guide 104 can be deflected by shaping the deflection location 102. The inner guide 104 advantageously includes a pre-shaped distal end 116 providing an optimized geometry for locating specific vascular features (the coronary sinus ostium, for example). As shown in FIG. 1B, the pre-shaped distal end 116 includes a curve 106.

A combination of the pre-shaped distal end 116, the extensibility of the inner guide 104, and/or the adjustability of the outer guide 101 at deflection location 102 provides an improved and flexible system for maneuvering the guide catheter within the venous system and constricted cardiac structures.

The maneuvering features of the present invention serve to reduce procedure time for finding and cannulating desired vessels. By way of example, one such procedure involves inserting the outer guide 101 through a percutaneous access vessel, such as the left cephalic vein. At this stage, the inner guide 104 may be retracted within the outer guide 101, such that the pre-shaped distal end 116 of the inner guide 104 is within the outer guide 101. The distal end 116 of the outer guide 101 is advanced to an access chamber, such as the right atrium.

Once the outer guide 101 has successfully reached an access chamber, the inner guide 104 is then extended. Extension of the inner guide 104 and adjustment of the outer guide deflection location 102 can be used in combination to navigate the distal tip 110 of the inner guide 104 to the vessel of interest.

In one embodiment, once the vessel is located, the outer guide 101 may be distally advanced over the inner guide 104 to seat the outer guide 101 in the subject vessel. In this embodiment, the inner guide 104 can then be proximally retracted until it is removed from the catheter 100, leaving the larger outer guide lumen 103 available for delivering a payload, such as a pacing lead, into the vessel of interest. In another embodiment, the inner guide 104 is left seated in the vessel of interest and a payload can be advanced through the inner guide 104 to the vessel of interest.

Although the catheter 100 of the present invention as described herein can be used for introducing pacing leads into heart vessels, there are other uses to which the catheter 100 may be adapted. For example, once the coronary sinus ostium is cannulated, an injection of a radioopaque dye may be delivered through the catheter 100 for purposes of mapping venous structures. During dye injection, blood flow in the vessel may require occlusion. An occlusion balloon pre-installed on a distal section of the catheter 100 may be used to occlude blood flow. Also, the catheter may include distally mounted electrodes for obtaining ECG readings.

Various features of a catheter in accordance with the present invention will now be described in greater detail, starting with the outer guide 101. In one embodiment, the cross sectional shape of the outer guide 101 is substantially annular with an outer diameter between about 5 French and about 10 French. The length of the outer guide 101 can range from about 25 to about 75 centimeters. For purposes of cannulating the coronary sinus through the right atrium via the superior vena cava, for example outer guide lengths from about 35 to about 55 centimeters suffice for accessing many cardiac features of interest via this pathway.

The outer guide 101 typically has sufficient flexibility to allow a clinician to navigate convoluted vasculature, with the guide 101 still having sufficient axial stiffness to be pushed from the proximal end to an internal destination. The outer guide 101 may be fabricated from extruded polymeric tubing. To achieve superior axial stiffness, a tubing with multi-layer walls is desirable. In one embodiment, and as shown in FIG. 1C, the outer guide layers include a smooth elastomeric casing 114 (e.g. high durometer Pebax), a stainless steel braid 115, and an inner lubricious lining 112 formed, for example, from PTFE. The stainless steel braid stiffens the proximal portion of the outer guide 101 so the outer guide 101 minimally deflects under normal axial loads. In one particular embodiment, the distal section of the outer guide 101 has greater flexibility than the proximal end, with a transition in flexibility occurring near the preformed deflection location 102. Such an outer guide design can employ any combination of varying geometry (diameter, wall thickness) and/or varying wall materials to accomplish a desired change in flexibility at the deflection location 102.

As is further shown in FIG. 1C, the outer guide 101 further includes a steering mechanism 109 to control the shape of the deflection location 102. FIG. 1C is a cross sectional view of the catheter of FIG. 1B further showing a steering tendon 109 disposed within an extruded cavity 113 within the wall of the outer guide 101. The steering tendon 109 shown in FIG. 1C is configured as a circular wire, although any elongated, tensile load bearing member with a given cross sectional shape can perform this function, such as a ribbon with an elongated rectangular profile for example.

Embedding the tendon 109 in the extruded cavity 113 advantageously provides a conduit for radially restraining the tendon 109 along the catheter length, yet allows the tendon 109 to freely travel longitudinally. Further, the extruded cavity 113 for containing the tendon 109 allows the inner and outer surfaces of the outer guide 101 to remain relatively smooth.

Alternative configurations may include tendons 109 movably disposed within the outer guide lumen 103, and such configurations are feasible given sufficient geometric clearances. Various alternative methods of disposing a steering member 109 within catheter lumens are known in the art.

In other embodiments, a number of steering tendons 109 can be disposed as previously described, allowing for any combination of greater tendon tensile strength, tendon redundancy, and/or multiple deflection modes of the preformed distal end 117.

Turning now to FIG. 2A, a deflection action of the outer guide 101 at the catheter's distal end is illustrated. The outer guide 101 deflection includes an adjustable bend angle 201. The angle 201 is shown measured between the undeformed centerlines of the outer guide 101 both proximal and distal to the predetermined location 102. The undeformed centerlines are representative features of the outer guide 101 and are derived by assuming the flexible outer guide 101 is held substantially straight proximally and distally to the predetermined deflection location 102, and forming a line through the cross sectional centroid of the outer guide 101.

The action of the steering tendon 109 is such that applying a tensile force to the proximal end of the tendon 109 causes an increased bend angle 201. Releasing the tensile force from the steering tendon causes a decreased bend angle 202. The new shape of the catheter's distal end resulting from bend angles 201 and 202 are shown in FIG. 2A with solid and phantom lines, respectively.

Figure 5:
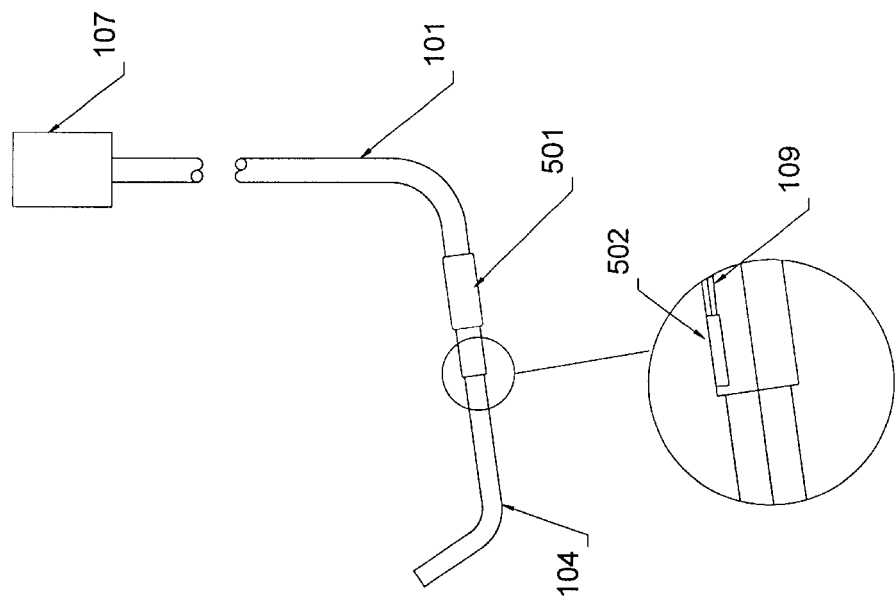
FIG. 5 is a view of the distal end of the catheter showing a steering attachment and an occlusion balloon.

It will be apparent to those skilled in the art that the predetermined deflection location 102 can be formed by selecting an appropriate steering attachment point on the outer guide 101 distal to the deflection location 102, as is best shown in FIG. 5, and creating one or more structural features at the deflection location 102. For example, such structural features can include, alone or in combination, a pre-shaped bend, a guide wall pre-stress, or an abrupt change in outer guide stiffness. The optimal structural feature to be used will depend on the composition of the outer guide 101 and the allowable deformation of a transverse cross section at the deflection location 102.

The shape of the predetermined deflection location 102 when no axial force is applied to the steering tendon is chosen based on expected venous pathways to be accessed by a catheter 100 implemented in accordance with the principles of the present invention. In certain circumstances, it may be desirable for the distal end 117 of the outer guide 101 to remain substantially straight (corresponding to zero degrees bend angle) at the deflection location 102 until the steering tendon 109 is activated.

In one embodiment, the deflection location 102 includes a preformed bend formed to correspond to a known venous pathway, and advantageously requires only minimal adjustments of the steering tendon 109 to account for varying anatomy or other structural anomalies. In such a case, the deflection location 102 can be defined by an initial bend angle and an initial bend radius. In various useful embodiments, the initial bend angle can range from about 0 to about 90 degrees. In cases where the bend angle is greater than 0 degrees, the initial bend radius is preferably greater than about six times an outer diameter of the outer guide 101. The preferred range of adjustment of the outer guide 101 bend angle is from 0 to about 150 degrees.

With respect to FIG. 2B, an illustration of preformed bend radii at the deflection location 102 is shown. Bend radius 203 is smaller than bend radius 204, both bend radii in FIG. 2B corresponding to approximately the same bend angle. The shapes of the outer guide 101 with respect to bend radii 203 and 204 are shown in solid and phantom lines, respectively. The bend radii 203 and 204 are measured on the outer surface of the outer guide 101 and with respect to the inner curve of the bend. The bend radius of the predetermined deflection location will likely change depending on the bend angle as tension is applied to the steering tendon 109. Those skilled in the art can appreciate that the various structural features that are included at the deflection location 102 will influence the initial, unstressed bend radius, as well as the size of the bend radius, as deflection is changed via the steering tendon 109.

Turning now to an embodiment of the inner guide 104, and with reference to FIGS. 1B and 1C, the inner guide 104 typically has an outer diameter that is about 4 French to about 10 French. The outer diameter of the inner guide 104 is preferably sized to facilitate free movement of the inner guide 104 within the outer guide 101. The inner guide 104 may be fabricated from an extruded polymer tube.

Another configuration is shown in FIG. 1C, where the outer guide 101 is fabricated from a multi-layer tubing. The layers of the multi-layer tubing can include a smooth elastomeric casing 114, a stainless steel braid 115, and an inner lubricious lining 112 on the inner surface. The curve 106 at the pre-shaped distal end 116 may be molded or thermoset after extrusion. In catheters where the inner guide 104 first finds the destination vessel, and then the outer guide 101 is slid over the inner guide 104, a relatively stiff inner guide 104 is typically desired. In cases where the inner guide 104 cannulates the destination vessel and the payload is fed through the inner guide 104, a more flexible inner guide 104 with a thinner wall may be desirable.

Figure 3B:
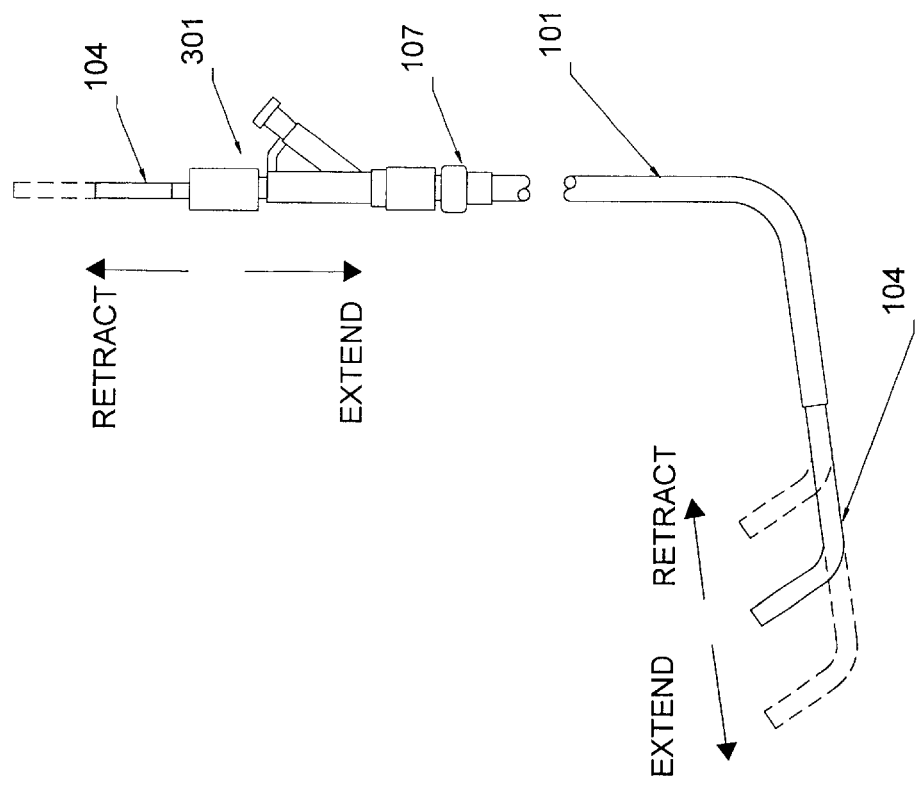
FIG. 3B is a cutaway view of the distal tip of the catheter illustrating the inner guide fully retracted within the outer guide.
Figure 3A:
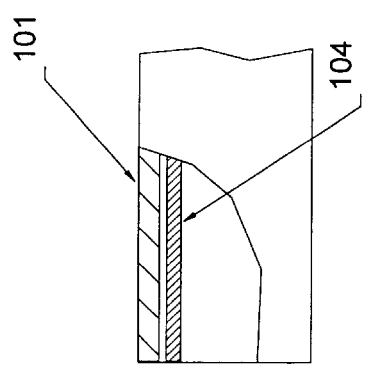
FIG. 3A is a view of the distal end of the catheter showing extension and retraction of an inner guide.

Turning to FIG. 3A, an embodiment of the present invention is illustrated in which the inner guide 104 is deformable and retractable within the outer guide 101. These characteristics advantageously allow the catheter 100 to assume different distal end shapes when the inner guide 104 is retracted and extended. The final extended and retracted shapes depend on the dimensions of the pre-shaped distal end 116 of the inner guide 104, the dimensions of the pre-determined deflection location 102, and the relative flexibility of the inner and outer guides 104, 101.

In one configuration, the inner guide 104 is deformable and less stiff than the outer guide 101. This enables the inner guide 104 to be fully retractable within the outer guide 101, and allows the catheter's distal end to assume the shape of the outer guide distal end 117 when the inner guide 104 is retracted. Such a configuration is advantageous when attempting to cannulate the coronary sinus.

For example, when the inner guide 104 is retracted, the catheter 100 has a broadly curved distal end when navigating from the superior vena cava into the right atrium. After the distal end reaches the right atrium, the inner guide 104, which has a much sharper pre-formed bend, is extended. This sharper bend of the inner guide 104 offers a more optimal geometry for finding the coronary sinus ostium from the right atrium. The inner guide 104 is typically extendable by at least 2 cm, and more desirably by 5 to 15 centimeters for right atrium use. For other applications, an extension range of at least 0 to 20 centimeters may be desirable.

FIG. 3B further illustrates the longitudinally displaceable inner guide 104. The inner guide 104 is drawn with solid lines and is shown in an initial position relative to the outer guide 101. The inner guide 104 is further drawn in phantom lines to illustrate the advantageous change of catheter distal tip shape when extension and retraction of the inner guide 104 is combined with a preformed distal tip of the inner guide 104 and a deflection location on the outer guide 101.

Figure 4B:
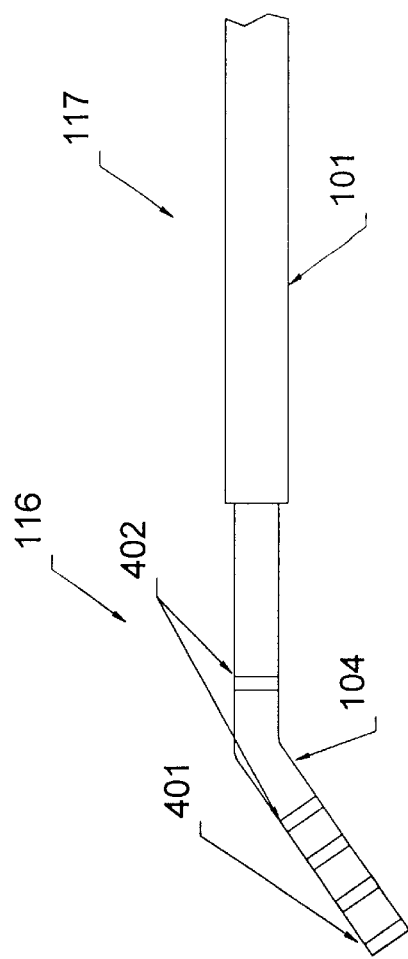
FIG. 4B is a view of the distal end of the catheter showing end electrodes and band electrodes provided at the distal ends of the inner guide.
Figure 4C:
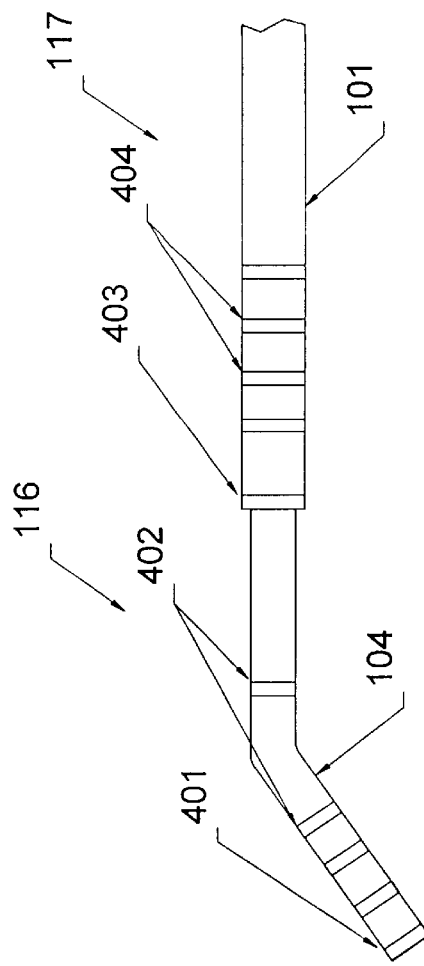
FIG. 4C is a view of the distal end of the catheter showing end electrodes and band electrodes provided at the distal ends of the inner and outer guides.
Figure 4A:
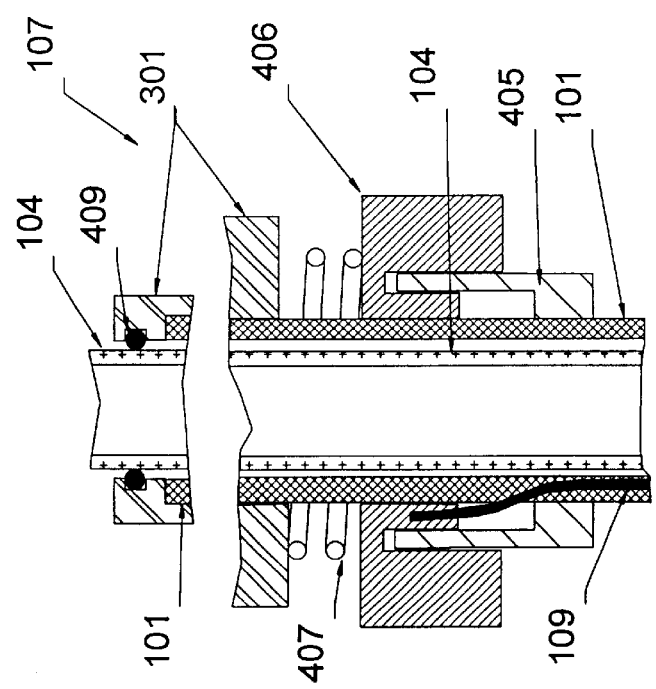
FIG. 4A is a cross sectional view of an embodiment of an actuator mechanism of the guide catheter.

Turning now to FIG. 4A, an embodiment of the actuator 107 provided at the proximal end of the catheter 100 is illustrated. In this embodiment, the steering tendon 109 is terminated outside the outer guide 101 and connected to a slideable member 406. Applying a proximal force to slideable member 406 imparts a tensile force to the steering tendon 109. In this embodiment, the actuator 107 further includes a stopping member 405 that is affixed to at least the outer guide 101. The stopping member 405 acts to prevent distal overtravel of the sliding member 406.

Further embodiments of the stopping member 405 can include a locking arrangement to prevent axial rotation of the slideable member 406. Yet another embodiment of the stopping member 405 includes a longitudinal locking arrangement to selectably enable and disable longitudinal translation of the slideable member 406. Locking the slideable member 406 enables the actuator 107 to adjust and then set the shape of the tip deflection 102 to a fixed angle. A spring 407 is optionally disposed between the sliding member 406 and the actuator 107 to allow automatic return of the slideable member 406 to the stopping member 405 upon release of the slideable member 406.

Those skilled in the art will understand that various mechanisms can be used in place of the slideable member 406, such as levers, screws and pull tabs, all of which allow transmittal of axial force to the steering tendon 109. Further, it is appreciated that multiple structural members can be incorporated into the actuator 107 to act on a plurality of steering tendons 109 if so desired.

In the case of the embodiment shown in FIG. 4A, the slideable member 406 can include multiple slide members distributed around the perimeter of the outer guide 101, each slideable member 406 connected to a separate steering tendon 109. In such an embodiment, each slideable member 406 can independently apply axial forces to its associated steering tendon 109, allowing for greater control of the deflection location 102.

A hemostatic valve 301 may be included as part of the actuator 107. The hemostatic valve 301 is a standard catheter termination device, such as a Model 23242/5 manufactured by Guidant Corporation, and is well known in the art. In one embodiment, a rotateable hemostatic valve 301 connects to both inner and outer guides at the catheter's proximal end, and the proximal end of the inner guide 104 protrudes from the proximal end of the hemostatic valve 301. In this manner, the proximal end of the inner guide 104 is accessible for manipulation. For example, applying a longitudinal force on the proximal end of the inner guide can allow extension and retraction of the inner guide 104, as illustrated in FIG. 3B. The hemostatic valve 301 includes a seal 409 between the inner and outer guides 104, 101. The body of the hemostatic valve 301 can also serve as a grip from which to rotate the outer guide 101. Turning now to FIG. 4B, there is illustrated an embodiment of a catheter employing an end electrode 401 and band electrodes 402 on the inner guide 104. Although embodiments of the present invention are directed to guiding applications, it is a commonly desired to obtain ECG readings during implantation of pacing devices or for other coronary access procedures. FIG. 4C shows another embodiment of the catheter 100, where an end electrode 403 and band electrodes 404 are disposed on the distal end 117 of the outer guide, the inner guide 104 further including electrodes 401 and 402 disposed as previously described. The electrodes are mounted flush with the guide outer surfaces and soldered or welded to one or more internally disposed electrical conductors. The composition, number, and dimensions of electrodes may be chosen in a manner well known in the art for various applications. The deployment of electrodes is typically dependent on the desired distal geometry of the catheter and the lumen clearances needed to run conductors through one or both of the inner and outer guides 104, 101.

Referring again to FIG. 1C, which shows a cross section near the distal end of the catheter, the inner guide 104 is shown centrally disposed within the outer guide 101. The inner guide has an open lumen 105. Disposed within the lumen 105 are electrical conductors 108 which are connected to the electrodes 401, 402, 403, and 404 and a pacing lead 118. In one configuration, the electrical conductors 108 are disposed within the outer lumen 103. In another configuration, the conductors 108 may be embedded within the walls of one or both of the inner guide 104 and the outer guide 101. Those skilled in the art will appreciate that embodiments of the invention can allow any combination of the described methods of disposing the electrode wires, limited by practical limitations due to the geometry of the guides 101 and 104, wires 108 and payload 118.

Turning now to FIG. 5, details near the outer guide distal tip 111 are illustrated where a steering tendon 109 is attached. In this embodiment, the steering tendon 109 is attached near the distal tip of the outer guide 101. An interface member 502 connects to both the steering tendon 109 and outer guide 101 for purposes of transmitting and distributing tensile force to the outer guide 101. One configuration of the interface member 502 can include a semicircular stainless steel ring welded or soldered to the steering tendon 109. The interface member 502 can be attached to the outer guide 101 by bonding or embedding the member into the inner surface of the outer guide 101.

In FIG. 5, an occlusion balloon 501 is shown attached to a distal section of the outer guide 101. During pacing lead implantation, it may be required to occlude blood flow when injecting a radio-opaque dye for purposes of venography. In this embodiment, the outer guide 101 would be seated in a location where a venograph is desired, the balloon 501 inflated, and a dye injected via the inner guide 104 or outer guide 101 as appropriate. This advantageously allows venography during an implant procedure without having to remove the outer guide 101. The design of the occlusion balloon 501 and the inflation means for the balloon 501 are well known in the art.

Turning to FIG. 6A, the delivery of a payload is shown for purposes of illustration. In this case, a pacing lead 118 represents the payload. In other embodiments of the inventions, the payload can include a radio-opaque dye or an ablation device. In the embodiment of FIG. 6A, the inner guide 104 has been removed by the clinician during the procedure, and the payload 118 can be seated within a coronary vessel via the outer guide 101. Alternatively, for a smaller payload or given larger inner guide diameter, the embodiment of FIG. 6B can be used. In this configuration, the inner guide 104 is left in place once it has cannulated the coronary sinus and the inner guide 104 provides the guiding pathway for the payload 118.

It will, of course, be understood that various modifications and additions can be made to the preferred embodiments discussed hereinabove without departing from the scope of the present invention. For example, although the present invention is particularly useful in providing percutaneous access to the coronary sinus ostium via the right atrium, it can be appreciated by one skilled in the art that the present invention is useful in a multitude of guiding catheter applications. Accordingly, the scope of the present invention should not be limited by the particular embodiments described above, but should be defined only by the claims set forth below and equivalents thereof.

What is claimed is:

1. A catheter, including:
    an outer guide including an outer guide lumen, a distal end, a proximal end, and a predetermined deflection location proximate the distal end;

an occlusion balloon affixed to the distal end of the outer guide;

an inner guide including an inner guide lumen, a pre-formed distal end, and a proximal end, the inner guide movable within the outer guide lumen and displaceable beyond the distal end of the outer guide; and an actuator mechanism located at a proximal end of the catheter, the actuator mechanism changing a bend angle at the predetermined deflection location of the outer guide, and the proximal end of the inner guide accessible at the proximal end of the catheter allowing adjustable axial displacement of the pre-formed distal end of the inner guide relative to the distal end of the outer guide.

2. A catheter according to claim 1, wherein at least 2 centimeters of the inner guide can be axially displaced beyond the distal end of the outer guide.

3. A catheter according to claim 1, wherein the inner guide can be axially displaceable beyond the distal end of the outer guide within a range of 0 centimeters and about 20 centimeters.

4. A catheter according to claim 1, wherein the pre-formed distal end of the inner guide is deformable such that the inner guide is retractable within the distal end of the outer guide.

5. A catheter according to claim 1, wherein the bend angle is defined relative to a longitudinal axis of the outer guide proximal to the predetermined deflection location.

6. A catheter according to claim 5, wherein the bend angle is adjustable from a minimum angle of about 0 degrees to a maximum angle of about 150 degrees.

7. A catheter according to claim 1, wherein a bend radius of the predetermined deflection location is greater than about six times an outer diameter of the outer guide.

8. A catheter according to claim 1, wherein axial forces exerted on the proximal end of the inner guide respectively extend and retract the pre-formed distal end of the inner guide relative to the distal end of the outer guide.

9. A catheter according to claim 1, further including at least one steering tendon connected to the inner guide proximate to the pre-formed distal end.

10. A catheter according to claim 9, wherein the actuator mechanism produces a tensile force acting on the at least one steering tendon to impart a change in the bend angle at the predetermined deflection location of the outer guide.

11. A catheter according to claim 1, further including at least one steering tendon connected to the outer guide proximate to the distal end.

12. A catheter according to claim 11, wherein the actuator mechanism produces a tensile force acting on the at least one steering tendon to impart a change in the bend angle at the predetermined deflection location of the outer guide.

13. A catheter according to claim 1, wherein an axial rotational force imparted on the proximal end of the outer guide rotates the pre-formed distal end of the inner guide.

14. A catheter according to claim 1, wherein one of the inner guide and outer guide is configured to transport an injectable dye.

15. A catheter according to claim 1, further including a seal between the inner guide and the outer guide.

16. A catheter according to claim 1, further including:

an electrode located at distal end of at least one of the inner guide and outer guide; and an electrical conductor coupled to the electrode, the electrical conductor extending through the inner guide or outer guide to a proximal section of the catheter.

17. A catheter according to claim 1, further including:

a plurality of band electrodes disposed at a distal section of at least one of the inner and outer guides; and at least one electrical conductor connected to the band electrodes, the at least one electrical conductor extending through the inner guide or outer guide to a proximal section of the catheter.

18. A catheter, comprising:

an outer guide including an outer guide lumen, a distal end, a proximal end, and a predetermined deflection location proximate the distal end;

an occlusion balloon affixed to the distal end of the outer guide;

an inner guide, the inner guide movable within the outer guide lumen and displaceable beyond the distal end of the outer guide, the inner guide comprising:

an inner guide lumen, the inner guide lumen dimensioned to receive a cardiac lead;

a distal end having a pre-formed deflection proximate the distal end; and a proximal end; and an actuator mechanism located at a proximal end of the catheter, the actuator mechanism changing a bend angle at the predetermined deflection location of the outer guide, and the proximal end of the inner guide accessible at the proximal end of the catheter allowing adjustable axial displacement of the distal end of the inner guide relative to the distal end of the outer guide.

19. The catheter of claim 18, wherein the inner guide lumen is dimensioned to receive a cardiac lead configured for implantation in a coronary sinus of a heart of a patient.

20. The catheter of claim 18, wherein the inner guide lumen is dimensioned to receive a cardiac pacing lead configured for implantation in a coronary sinus of a heart of a patient.

21. A catheter according to claim 18, wherein the pre-formed distal end of the inner guide is deformable such that the inner guide is retractable within the distal end of the outer guide.

22. A catheter according to claim 18, wherein the bend angle is defined relative to a longitudinal axis of the outer guide proximal to the predetermined deflection location, wherein the bend angle is adjustable from a minimum angle of about 0 degrees to a maximum angle of about 150 degrees.

23. A catheter according to claim 18, further including at least one steering tendon connected to the outer guide proximate to the distal end.

24. A catheter according to claim 23, wherein the actuator mechanism produces a tensile force acting on the at least one steering tendon to impart a change in the bend angle at the predetermined deflection location of the outer guide.

* * * * *